United States Patent [19]

LaVallo et al.

[11] Patent Number: 5,000,738
[45] Date of Patent: Mar. 19, 1991

[54] PROTECTIVE SYRINGE WITH FRANGIBLE BARREL

[76] Inventors: Frank LaVallo, 3319 Lantern Trail; W. M. Patterson, 1003 Breckenridge Dr.; Ray F. Ontko, 4539 Esteb Rd., all of Richmond, Ind. 47374

[21] Appl. No.: 350,547

[22] Filed: May 11, 1989

[51] Int. Cl.⁵ .............................................. A61M 5/50
[52] U.S. Cl. ..................................... 604/110; 604/195
[58] Field of Search ............... 604/110, 192, 194, 195, 604/263; 128/763, 919

[56] References Cited

U.S. PATENT DOCUMENTS

| | | | |
|---|---|---|---|
| 4,026,287 | 5/1977 | Haller | 128/215 |
| 4,474,830 | 5/1988 | Gloyer | 604/110 |
| 4,592,744 | 6/1986 | Jagger et al. | 604/192 |
| 4,692,156 | 9/1987 | Haller | 604/195 |
| 4,770,655 | 9/1988 | Haber et al. | 604/110 |
| 4,790,822 | 12/1988 | Haining | 604/110 |
| 4,808,169 | 2/1989 | Haber et al. | 604/195 |
| 4,861,338 | 8/1989 | Mathiesen et al. | 604/110 |
| 4,874,382 | 10/1989 | Lindemann et al. | 604/195 |
| 4,950,251 | 8/1990 | Haining | 604/195 |

*Primary Examiner*—John D. Yasko
*Assistant Examiner*—Adam J. Cermak
*Attorney, Agent, or Firm*—Barnes & Thornburg

[57] ABSTRACT

A syringe is provided for injecting pharmaceuticals into patients and withdrawing liquid samples from patients. The syringe includes a barrel having proximal and distal ends. A plunger is reciprocably disposed in the barrel to drive fluid from the distal end when moving in that direction. The syringe further includes an end wall for closing the distal end, a cannula on the end wall, and an assembly for connecting the end wall to the plunger so that movement toward the proximal end of the barrel will move the cannual within the barrel. A frangible section provides a sealed connection between the end wall and the distal end of the barrel. The plunger is proportioned and shaped to engage the end wall and break the frangible section when the plunger is pushed toward the distal end of the barrel with a predetermined force.

29 Claims, 2 Drawing Sheets

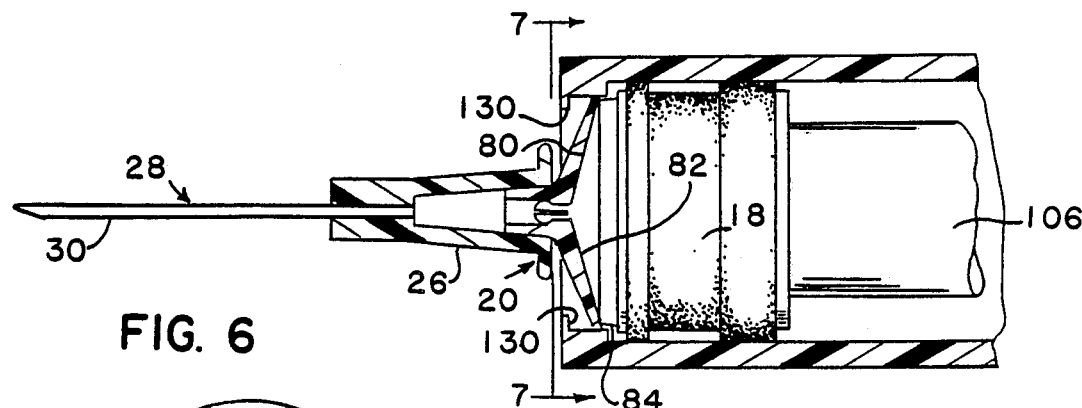
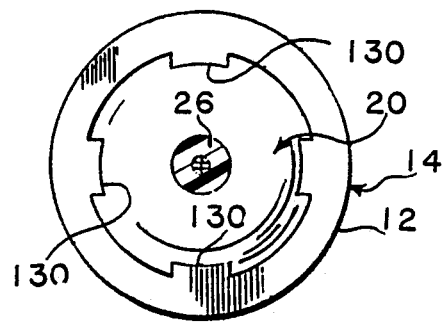
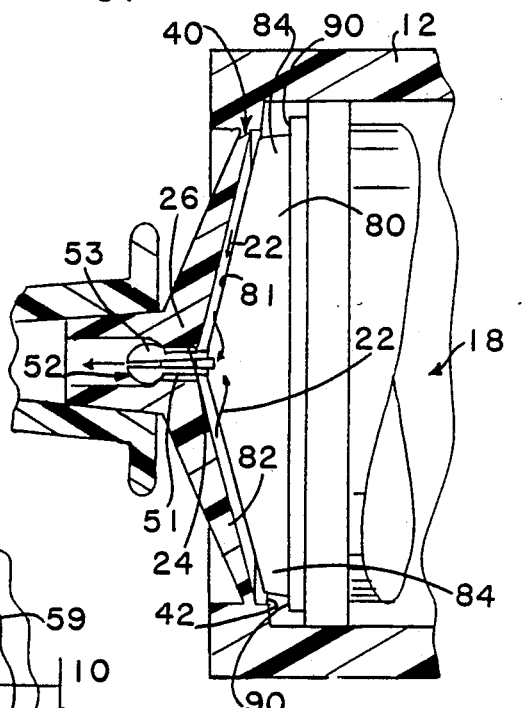
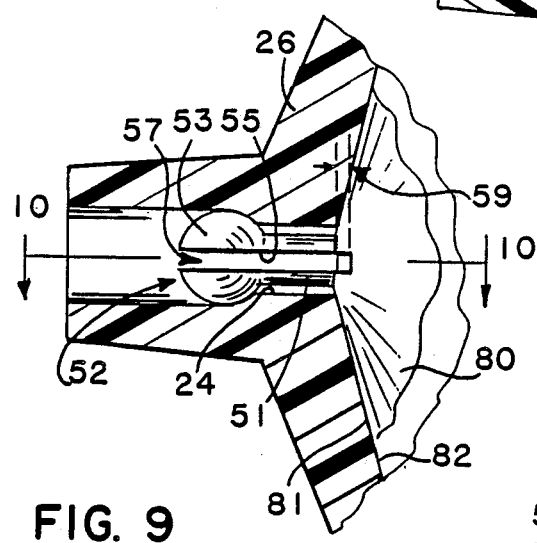
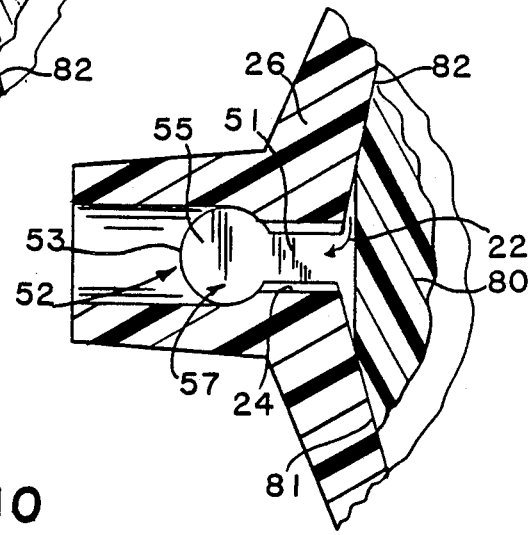

PROTECTIVE SYRINGE WITH FRANGIBLE BARREL

BACKGROUND AND SUMMARY OF THE INVENTION

The present invention relates to syringes of the type which are used for injection of pharmaceuticals into patients and sometimes for withdrawing liquid samples from patients. More particularly, the present invention relates to the provision of an improved syringe constructed such that, once it has been used, it can be easily manipulated to retract the rather sharp cannula to be entirely disposed within the barrel of the syringe in a point protective position. The manipulation of the cannula breaks the syringe barrel such that the syringe cannot thereafter be used.

With the threat of AIDS and hepatitis infection becoming a major concern, medical personnel must take extra precautions not to prick themselves with the cannula point of a syringe, particularly a syringe which has been used on a patient. Presently, once a syringe is used, medical personnel are required very carefully to place a protective cover back over the cannula or to drop the syringe into a "safe depository" system. This act of replacing the protective cover back over the cannula is dangerous. Further, it is difficult and expensive to provide safe depository systems at all locations where syringes are used.

It is known to provide a syringe having features designed to protect users from inadvertent needle pricks or other harm. See, for instance, U.S. Pat. Nos. 2,473,733; 2,888,923; 2,925,083; 2,972,991; 3,306,290; 3,356,089; 3,820,652; 4,026,287; 4,507,117; 4,592,744; 4,692,156; 4,710,170; 4,747,830; 4,790,822; and 4,804,370.

Our inventive syringe, however, is the first syringe designed to have a frangible end wall portion or an end wall means connected to the syringe barrel by a frangible portion such that continued movement of the plunger after the syringe contents are expelled with a predetermined higher force application will break the frangible portion to separate the cannula from the barrel so that the cannula can then be retracted into the barrel.

It is an object of our invention, therefore, to provide a syringe which is constructed such that, once it is used with a patient, it can be easily and safely manipulated by medical personnel to break the syringe and retract the cannula entirely within the barrel of the syringe such that the cannula point will not thereafter be available to injure anyone including the medical personnel further handling the syringe. Our invention is noteworthy because it is economical to produce and will not substantially increase the cost of a syringe.

It is a further object of our invention to provide such a syringe comprising a barrel having a proximal end and a distal end, a plunger reciprocably disposed in the barrel to drive fluid from the distal end when moving in that direction and end wall means for closing the distal end of the barrel. The end wall means may preferably be formed as a part of the syringe barrel with a defined frangible portion designed to be broken by the pushing action of the plunger after the contents have been fully injected A cannula may be mounted on the end wall means for the barrel in a conventional manner Then, we provide means for connecting the end wall means to the plunger such that, movement of the plunger toward the proximal end will move the end wall means and cannula within the barrel to what we refer to as a point protective position.

It is still another object of our invention to provide such an end wall means which includes an annular frangible portion providing a connection between the end wall means and the barrel This frangible portion will be broken when the plunger is pushed toward the barrel distal end with a pushing force significantly higher than required to inject the contents of the syringe. The plunger may preferably be proportioned and shaped to have an annular shoulder to engage and break the annular frangible portion when the plunger is pushed toward the distal end a predetermined amount beyond that required fully to inject the contents.

The following objects further summarize the advantages of our invention:

To provide an improved anti-needle stick, anti-drug abuse syringe which uses industry standard cannula fixtures in which the cannula point is retracted into the barrel of the syringe after use of the syringe, and in which the syringe is no longer useful after its initial use.

To provide such a syringe in which the cannula is locked in its point protective position within the barrel.

To provide such a syringe which requires little additional manipulation to properly operate the syringe, relative to conventional syringes.

To provide such a syringe which may be used in pre-filled and non-filled applications. To provide such a syringe which allows multiple needles to be mounted and used during a single use of the syringe. In some applications, for example, a relatively large diameter needle is used to draw product into the syringe, this larger needle is removed and disposed of and replaced with a needle of relatively small diameter, and product is injected in one or more injections using this smaller needle. It should be noted that the first needle is used only to draw product into the syringe and is not therefore contaminated.

To provide such a syringe which has a smooth inner bore to eliminate air entrapment and provides a reliable means of expelling air which may have been introduced during filling.

To provide such a syringe which allows for substantially complete injection of fluid, minimizing waste of and improving accuracy of measurement of product.

To provide such a syringe which has minimal part count to improve ease of manufacture and sterility.

To provide such a syringe which has substantial means of preventing unintentional recantation of needle, as during impingement with bone or other hard materials.

To provide such a syringe in which the plunger may move through the barrel to deliver the product in a smooth, controlled motion without sudden movement or jarring of the needle which might alarm the patient or damage tissue Such sudden movement or jarring might be caused, for example, by a snap fitting which is sometimes used as a means for engaging the needle or closing means with the plunger or retracting means.

To provide such a syringe in which the operator of the syringe receives tactile feedback indicating complete injection.

To provide such a syringe in which the syringe must be manipulated in an intentional manner in order to separate the end wall means from the barrel.

Other objects, features, and advantages of the present invention will become apparent as this specification progresses.

BRIEF DESCRIPTION OF THE DRAWINGS

The detailed description particularly refers to the accompanying figures in which:

FIG. 6 is a fragmentary sectional view showing an alternative embodiment utilizing peripherally spaced lugs to retain the end wall after it is broken;

FIG. 7 is a view taken along lines 7—7 in FIG. 6;

FIG. 8 is an enlarged sectional view of a portion of the end wall means of FIG. 1 showing fluid being expelled from the syringe chamber through an axially extending slot formed in the connecting ball and stem assembly attached to the plunger as the contoured surface of the plunger is moved to approach the end wall means;

FIG. 9 is an enlarged view similar to FIG. 8 showing mating engagement of the contoured surface of the plunger and the end wall means; and FIG. 10 is a transverse sectional view taken along lines 10—10 of FIG. 9 showing a cross-sectional view of the axially extending slot.

DETAILED DESCRIPTION OF THE DRAWINGS

Figure 1:
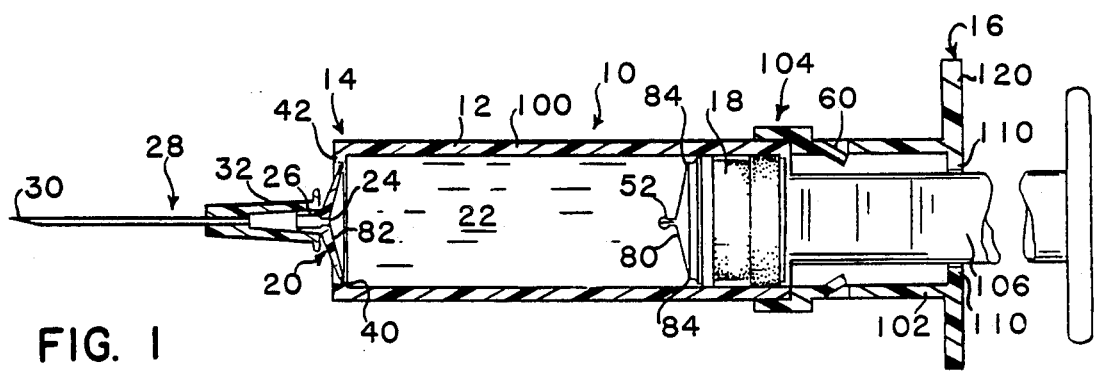
FIG. 1 is a sectional view of the illustrative syringe of the present invention.

Turning to the drawings, it will be seen that we have illustrated a syringe 10 comprising a cylindrical barrel 12 having a distal end 14, a proximal end 16 and a plunger 18 reciprocably disposed within the barrel 12 such that movement of the plunger toward the distal end 14 will push the pharmaceutical material out the distal end. This distal end 14 of the barrel 12 is provided with end wall means 20 for containing the fluid 22 between the plunger 18 and the distal end. The illustrative end wall means 20 is provided with a concentric central passageway 24 disposed within a concentric, axially extending tapered hub 26.

A cannula 28 having a conventional sharpened point 30 is provided with a fitting 32 which conventionally fits over the hub 26. It will be appreciated that, within the scope of our invention, any number of different techniques may be used for fastening a cannula to the central portion of the end wall means 20 of the barrel 12.

Figure 4:
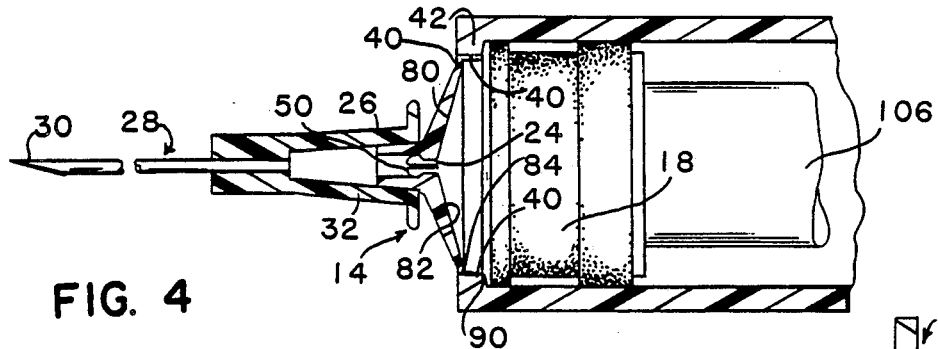
FIG. 4 is another fragmentary sectional view showing the plunger being used to break the frangible portion of the end wall means.
Figure 5:
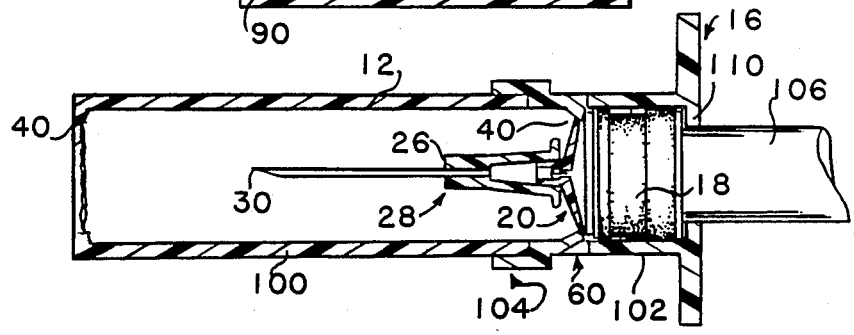
FIG. 5 is a sectional view showing the plunger and cannula retracted entirely within the syringe barrel and locked in a retracted position.

In the illustrative embodiment, the end wall means 20 is integrally molded or formed when the barrel 12 is formed to have a weakened annular frangible portion 40 connecting the hub 26 to the barrel 12. This frangible portion 40 is illustrated as a very thin annular radially outer edge extending concentrically about the end wall means 20. As illustrated, this frangible portion 40 extends peripherally and outwardly to a thickened wall portion or abutment 42 serving as a rigid outer end wall section of distal end 14 of barrel 12. More specifically, as illustrated, this rather thin frangible portion 40 is the radially outer edge of the conically shaped end wall means 20. When this frangible portion 40 is pushed axially outwardly, i.e., to the left as shown in the drawings, the frangible portion will break as shown in FIGS. 4 and 5.

In the illustrative embodiment, this pushing and breaking activity is accomplished by pushing the plunger 18 to the left as shown in the drawings. In the illustrative embodiment, means for connecting the plunger 18 to the cannula 28 is provided by forming a first engaging means 50 on the end wall means 20 and a second engaging means 52 carried by the plunger 18. Illustratively, the second engaging means 52 is a resilient, axially slotted protrusion which engages into a socket provided by the first engaging means 50. Illustratively, the socket 50 is formed in the hub 26 in communication with passageway 24.

The protrusion 52 on the distal end of plunger 18 is configured to engage socket 50 formed in hub 26 and is shown best in FIGS. 8–10. Preferably, protrusion 52 includes a stem 51 projecting outwardly from the conically shaped distal end 80 of plunger 18 and a ball 53 at the distal end of stem 51. Protrusion 52 is formed to include a slot 55 extending in an axial direction from the conic end 80 of plunger 18 through the stem 51 and ball 53 to an open mouth 57 provided in the ball 53 as shown best in FIGS. 9 and 10.

It will be appreciated that conservation of certain liquid medicines is important because of the high unit cost per ounce of such medicine. Syringe 10 is configured to expel substantially all of the liquid medicine 22 contained in the syringe chamber during injection of such medicine into a patient so that unnecessary waste of scarce medicine is minimized. Specifically, the exterior wall 81 of the conically shaped distal end 80 is configured to mate with an opposing conically shaped interior wall 82 of hub 26. The opposing walls 81, 82 will be drawn closer together as the plunger 18 is pushed toward hub 26 to expel liquid medicine 22 from the syringe chamber into the hollow fitting 32 and cannula 28. Opposing walls 81, 82 cooperate to discharge liquid medicine 22 into hollow fitting 32 first through hub passageway 24 as shown, for example, in FIG. 2. Once hub passageway 24 becomes substantially occluded by the ball 53 and stem 51 upon engagement of protrusion 52 in socket 50, then any remaining liquid medicine 22 in the syringe chamber will be discharged into the hollow fitting 32 and cannula 28 via the liquid-conducting passageway through protrusion 52 provided by axially extending slot 55 as shown best in FIG. 8.

Advantageously, substantially all of the liquid medicine 22 extant in the syringe chamber will be discharged into the cannula 28 even after engagement of protrusion 52 in socket 50 to minimize unnecessary waste of scarce and costly medicine and thereby avoid shortcomings of conventional syringes wherein a measurable quantity of liquid medicine remains unused in the syringe chamber after operation of the plunger. It will be appreciated that the protrusion 52 can be formed to include a liquid-conducting passageway such as axially extending slot 55 even though protrusion 52 may have a socket-engaging shape that is different than the ball 53 and stem 51 shape illustrated in the drawings. An added advantage of axially extending slot 55 is that it permits the protrusion 52 to collapse radially inwardly to a limited degree in passageway 24 to improve snap engagement of protrusion 52 in hub socket 50 as shown for example in FIG. 8. Axially extending slot 55 is configured to extend at least to the interface between the wall-defining passageway 24 and conically shaped interior wall 81 and, as shown in FIGS. 9 and 10, may extend a short distance 59 into the syringe chamber.

Figure 2:
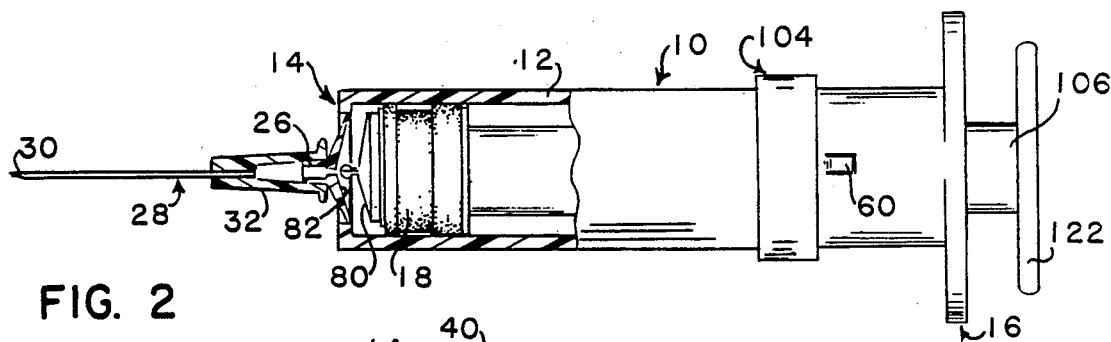
FIG. 2 is a sectional view of the illustrative syringe showing the plunger nearing the distal end to inject fluid from the syringe.
Figure 3:
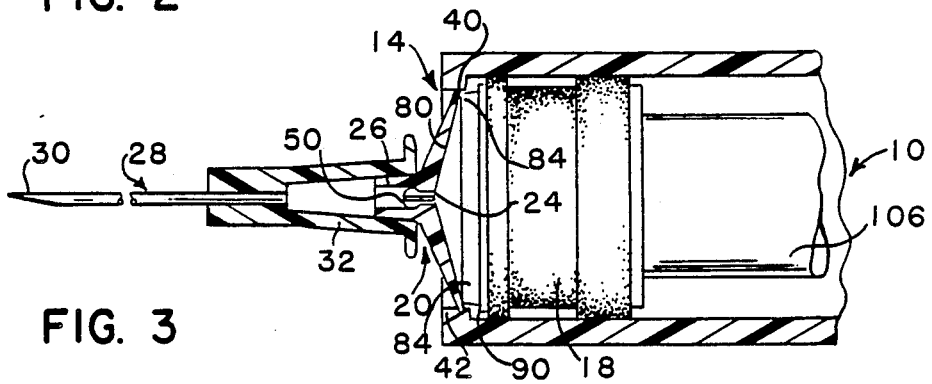
FIG. 3 is a fragmentary sectional view showing the plunger engaging the distal end wall means.

As shown in FIGS. 2 and 3, after the fluid is injected into the patient, further movement of the plunger 18 toward the distal end 14 will first connect the plunger 18 to the cannula 28 because the ball of the second engaging means 52 will engage into the socket of the first engaging means 50. The person administering the fluid to the patient can elect to disable the syringe after use by moving the plunger 18 still further toward the hollow fitting 32 and cannula 28 to break the frangible portion 40. This condition is illustrated in FIG. 4. Thereafter, retraction of the plunger 18 toward the proximal end 16 will dispose the cannula 28 entirely within the barrel 12 in what we refer to as a point 30 protective position. In the point protective position shown in FIG. 5, the plunger 18 is adjacent the proximal end 16 there to hold the end wall means 20 upon which the cannula 28 is mounted so that the cannula 28 is held entirely within the barrel 12 so that personnel will not be injured by the sharpened point 30.

So that the syringe will never again be used and the point 30 will not be projected beyond the distal end 14 of the barrel we provide one-way locking means 60 which will permit the plunger 18 to move toward the proximal end 16, but will not permit the plunger to move again toward the distal end 14 once the plunger moves to the right of the locking means to its FIG. 5 position. In the illustrative embodiment, the locking means 60 are integrally formed in the barrel 12 and turned inwardly to serve as the locking means.

In the illustrative embodiment, the plunger 18 is formed to accomplish several of the objectives of our invention. The illustrative plunger 18 has an exterior wall 81 on outwardly contoured end 80 that is shaped generally conformingly to fit against the axially inner surface 82 of the end wall means 20 substantially fully to expel fluid from the barrel 12 through the axially extending slot 55 when the plunger 18 is moved against the end wall means In the illustrative embodiment, both the contoured end 80 and the end wall means 20 surface 82 are shallow conical surfaces. The contoured surface 80 terminates at its radially outermost edge with an annular shoulder 84 which pushes against and breaks the frangible outer edge portion 40 as shown in FIGS. 3 and 4.

Axially inwardly and slightly outwardly from the shoulder 84, the plunger 18 is provided with a larger annular shoulder 90 which engages the abutment 42 to limit the movement of the plunger 18 toward the distal end 14 of the barrel 12. It will be appreciated that the engagement of this outer shoulder 90 against the abutment 42 limits the travel of the plunger 18 to the left as viewed in the drawings Before that limit is reached, the connection between the ball 52 and the socket 50 is made and the frangible portion 40 is severed. Thus, when the plunger 18 is retracted to the right as viewed in the drawings, the end wall means 20 and the cannula 28 mounted thereon is retracted to the proximal end 16 of the barrel 12 as shown in FIG. 5.

In the illustrative embodiment, the barrel 12 is formed to have a main body portion 100 and a proximal end portion 102 which are joined together as indicated at 104 by ultrasonic techniques or other conventional plastic joining techniques as shown in FIG. 1. Illustratively, the two portions 100, 102 may be joined together to capture the plunger 18 and its plunger stem 106 within the barrel 12. Any number of techniques may be utilized to capture the plunger 18 and its stem 106 within the proximal end portion 102 before connection is made at 104. In the illustrative embodiment, the end portion 102 is shown with radially inwardly extending flange means 110 which restricts the plunger 18 from moving to the right out of the proximal end 16 of the barrel 12. For ease in handling the syringe 10, the barrel 12 and its Proximal end portion 102 may be formed with wings as indiCated at 120 while the stem 106 may be provided with a small pushing member 122 which may be ultrasonically bonded or otherwise attached to the stem 106. The objective is to provide means for at least partially closing the proximal end 16 of the barrel 12 so that the plunger 18 is restrained from moving out of the barrel 12. Once the end wall means 20 is attached to the plunger 18, and the plunger 18 is moved to the right as shown in FIG. 5, then the plunger 18 and the end wall means 20 and cannula 28 connected thereto are trapped in the barrel 12 against further movement.

It will be appreciated that, within the scope of our invention, a number of different types of end wall means 20 may be used to close the distal end of the barrel 12. Instead of the frangible portion 40, for instance, we may provide an end wall which is formed separately from the barrel and merely disposed in some manner within the distal end of the barrel and connected to the barrel by some frangible means which is severed by the continued pushing action of the plunger 18 with a predetermined force. We may also provide any number of different types of connections between the plunger 18 and the end wall means 20 such that there can be a connection between the plunger and the end wall means to retract the cannula entirely within the barrel 12. Our invention, therefore, contemplates that the end wall means 20 upon which the cannula 28 is mounted will be adapted to be engaged and moved by the plunger 18 axially toward the proximal end 16 when it is time to retract the cannula to its point-protective position shown in FIG. 5. Also, we may use a variety of types of locking means 60 to hold the plunger 18, the end wall means 20 and the cannula 28 within the barrel 12.

Finally, the syringe of our invention may be used in a rather conventional fashion to draw liquid from a container into the barrel 12. Typically, the syringe will be manipulated so that the plunger 18 is moved against the distal end 14 and the cannula 28 will be inserted in the container of liquid When the plunger 18 is moved to the right as shown in the drawings, liquid will be drawn into the barrel 12 in a conventional manner. It will be appreciated that the configuration of protrusion 52 to include axially extending slot 55 acts to permit the maximum withdrawal of liquid from the container with minimum introduction of air into the syringe chamber during such liquid withdrawal. Little opportunity for entrapment of air exists because slot 55 provides a passageway through which any air extant in the syringe chamber can be expelled before liquid is withdrawn from the supply container and introduced into the syringe chamber via the cannula 28, fitting 32, and hub 26. Essentially, substantially all of the air extant in the syringe chamber can be discharged prior to filling the syringe with liquid because of the mating engagement of conic surfaces 81, 82 and the provision of "air exhaust" slot 55.

The syringe may be held generally upwardly with the cannula 28 sticking upwardly into the source of liquid. Movement of the plunger 18 upwardly (toward the distal end 14) will pump air back into the source container to increase air pressure in the container prior to fluid removal. The operator may tap the syringe to cause air bubbles trapped therein to move upwardly and out the passageway 24 in the cannula 28 to expel the air bubbles The Plunger 18 will be stopped at the desired location to establish a predetermined amount of injectable liquid in the syringe. At that point, the syringe is inserted into the patient and the plunger is moved further toward the distal end 14 to inject the liquid.

It will be appreciated that the liquid in the syringe will be substantially completely injected when the ball 52 engages into the socket 50 as shown in FIG. 3 of the drawing. At that point, the operator of the syringe will have a definite feel that the injection process is completed. The syringe will be removed from the patient at that point. Then, almost immediately, the same operator can push the plunger 18 with a predetermined force sufficient to sever the frangible portion 40 when the shoulder 84 engages the frangible portion. The operator will have a clear sense when that breaking the frangible portion occurs. Thereafter, retraction of the plunger 18 to its far right-hand position shown in FIG. 5 will pull the end wall means 20 and the cannula 28 safely within the barrel 12 leaving the distal end of the barrel broken open so that the syringe will no longer be useful.

In the embodiment shown in FIGS. 6 and 7, we provide means for retaining the end wall 20 after the frangible portion 40 is broken. The illustrative retaining means includes four peripherally spaced-apart, radially inwardly extending retainers 130 which prevent the end wall means from moving to the left as shown in FIGS. 6 and 7 after the frangible portion 40 is broken.

Advantageously, a syringe in accordance with the present invention can be used in the following manner without substantial risk of hazard to the user. The needle 28 is first inserted into a bottle containing a liquid to be disPensed. The liquid is withdrawn from the bottle using the plunger 18 without breaking the frangible collar 40 because movement of the plunger 18 away from the cannula 28 to fill the syringe will not cause the frangible collar 40 to rupture. The needle 28 can then be inserted into a patient and withdrawn without rupturing frangible collar 40 because, in part, the force necessary to accomplish puncture of the patient's skin and insertion of the needle 28 into the patient's body is not enough to break the frangible collar 40. For example, the syringe 10 is preferably configured so as to prevent rupture of frangible collar 40 while permitting needle recantation if the needle 28 hits a bone or the like when injecting painkillers during oral surgery Only at the election of the user is sufficient force applied to the plunger 18 to "push out" the hub 26 and break the frangible connection 40 to permit retraction of the needle 28, hollow fitting 32, and hub 26 into the syringe chamber to a locked position Although the invention has been described in detail with reference to certain preferred embodiments, variations and modifications exist within the scope and spirit of the invention as described and defined in the following claims.

What is claimed is:

1. A syringe comprising a barrel having a proximal end and a distal end, a movable plunger means reciprocably disposed in said barrel to drive fluid in said barrel toward and exiting out of said distal end when said plunger means is moved toward said distal end, end wall means for closing said distal end, a cannula means for said end wall means to permit said driven fluid to exit out said distal end, frangible means providing a sealed connection between said end wall means and said barrel distal end, said plunger means being proportioned and shaped to engage said end wall means and break said frangible means when said plunger means is moved toward said distal end with a predetermined force, means for connecting said end wall means to said plunger means such that movement of said plunger means toward said proximal end will move said cannula means on said end wall when said end wall is connected to the plunger means within said barrel and said end wall frangible connection has been broken and wherein movement of said plunger means toward said proximal end will open the connection between the plunger means and the end wall means if the end wall means has not had its frangible connection broken by movement of the plunger means toward the distal end.

2. The invention of claim 1 in which said connecting means includes first engaging means on said end wall means and second engaging means on said plunger means, said engaging means being adapted to be connected together by manipulation of said plunger means.

3. A syringe comprising a barrel having a proximal end and a distal end, a movable plunger means reciprocably disposed in said barrel to drive fluid in said barrel toward and exiting out of said distal end when said plunger means is moved toward said distal end, end wall means for closing said distal end, a cannula means for said end wall means to permit said driven fluid to exit out said distal end, means for connecting said end wall means to said plunger means such that movement of said plunger means toward said proximal end can move said cannula means on said end wall when said end wall is connected to the plunger means within said barrel, and frangible means providing a sealed connection between said end wall means and said barrel distal end, said plunger means being proportioned and shaped to engage said end wall means and break said frangible means when said plunger means is moved toward said distal end with a predetermined force; and wherein said second connecting means is formed to include a slot through which fluid is discharged from the barrel to the cannula means during movement of the plunger means toward said distal end.

4. The invention of claim 2 in which said barrel and plunger means are configured such that said cannula means can be retracted with said end wall means to be entirely disposed within said barrel to a protective position.

5. The invention of claim 4 including means for locking said cannula means in said point protective position within said barrel.

6. The invention of claim 1 in which said frangible means includes an annular frangible portion providing a connection between said end wall means and said barrel.

7. The invention of claim 6 in which said frangible portion is a weakened annular portion integrally formed between said barrel distal end and said end wall means.

8. The invention of claim 7 in which said connecting means includes cooperative engaging means on both said end wall means and said plunger means, which engaging means can be engaged by movement of said plunger means.

9. The invention of claim 8 in which said engaging means includes a socket formed on said end wall means and a protrusion for engaging said socket, said protrusion being provided on said plunger means.

10. A syringe comprising a barrel having a proximal end and a distal end, a movable plunger means reciprocably disposed in said barrel to drive fluid in said barrel toward and exiting out of said distal end when said plunger means is moved toward said distal end, end wall means for closing said distal end, a cannula means for said end wall means to permit said driven fluid to exit out said distal end, means for connecting said end wall means to said plunger means such that movement of said plunger means toward said proximal end can move said cannula means on said end wall when said end wall is connected to the plunger means within said barrel, and frangible means providing a sealed connection between said end wall means and said barrel distal end, said plunger means being proportioned and shaped to engage said end wall means and break said frangible means when said plunger means is moved toward said distal end with a predetermined force, wherein said frangible means includes an annular frangible portion providing a connection between said end wall means and said barrel, wherein said frangible portion is a weakened annular portion integrally formed between said barrel distal end and said end wall means, wherein said connecting means includes cooperative engaging means on both said end wall means and said plunger means, which engaging means can be engaged by movement of said plunger means, wherein said engaging means includes a socket formed on said end wall means and a protrusion for engaging said socket, said protrusion being provided on said plunger means and formed to include a slot through which fluid is discharged from the barrel during movement of the plunger means toward said distal end.

11. The invention of claim 1 including means for locking said cannula means in a retracted point protective position entirely disposed within said barrel.

12. The invention of claim 11 in which said locking means includes protrusions formed on said barrel adjacent said proximal end to engage said plunger means and hold it against movement toward said distal end.

13. A syringe comprising a plastic barrel, a proximal end integrally molded to said plastic barrel, a distal end, an outwardly contoured end wall means closing said distal end, and an annular frangible portion joining said end wall means to said distal end, a movable plunger means reciprocably disposed in said barrel to drive fluid in said barrel toward and exiting out of said distal end when said plunger means is moved toward said distal end, said end wall means further being molded to have an outwardly extending cannula mans hub with a central extending opening therethrough, a cannula means mounted on said hub to permit the driven fluid to exit out said distal end, said plunger means being formed to have an annular shoulder proportioned and shaped to engage said end wall means to break said frangible portion when said plunger means is moved toward said distal end with a predetermined force, and means for connecting said end wall means and said plunger means such that movement of said plunger means toward said proximal end will retract said end wall means and said cannula means within said barrel when said frangible portion has been broken and will disconnect the plunger means from said end wall when said frangible portion has not been broken.

14. The syringe of claim 13 in which said plunger means is further formed with an outwardly contoured end generally conformingly to fit within said end wall means substantially fully to expel fluid from the barrel when said plunger means is moved against said end wall means.

15. The syringe of claim 14 in which the connecting means is formed to include a passageway through which fluid is discharged from the barrel to the cannula means during movement of said outwardly contoured end of the plunger means toward engagement with the end wall means.

16. The syringe of claim 14 in which said plunger means contoured end is formed at its radially outer edge to define said annular shoulder.

17. The syringe of claim 14 in which said connecting means includes a first engaging means formed in said axially extending hub opening and a second engaging means provided generally on the center of said plunger means outwardly contoured end.

18. The syringe of claim 14 in which said connecting means includes a socket formed in said axially extending hub opening and a coacting projection for engaging said socket provided generally on the center of said plunger means outwardly contoured end.

19. A syringe comprising a plastic barrel, a proximal end integrally molded to said plastic barrel, a distal end, an outwardly contoured end wall means closing said distal end, and an annular frangible portion joining said end wall means to said distal end, a movable plunger means reciprocably disposed in said barrel to drive fluid in said barrel toward and exiting out of said distal end when said plunger means is moved toward said distal end, said end wall means further being molded to have an outwardly extending cannula means hub with a central extending opening therethrough, a cannula means mounted on said hub to permit the driven fluid to exit out said distal end, said plunger means being formed to have an annular shoulder proportioned and shaped to engage said end wall means to break said frangible portion when said plunger means is moved toward said distal end with a predetermined force, and means for connecting said end wall means and said plunger means such that movement of said plunger means toward said proximal end will retract said end wall means and said cannula means within said barrel when said frangible portion has been broken, wherein said plunger means is further formed with an outwardly contoured end generally conforming to fit within said end wall means substantially fully to expel fluid from the barrel when said plunger means is moved against said end wall means, wherein said connecting means includes a socket formed in said axially extending hub opening and a coacting projection for engaging said socket provided generally on the center of said plunger means outwardly contoured end, and wherein the coacting projection is formed to include a passageway through which fluid is discharge from the barrel to the cannula means during movement of said outwardly contoured end of the plunger means toward engagement with the end wall means.

20. The syringe of claim 18 in which said projection includes an axially projecting stem with a spherical ball carried at the distal end of said stem, said ball and stem having a slot therein dividing said ball into ball portions resiliently movable into said slot.

21. The syringe of claim 13 in which said barrel distal end is further formed with an annular, radially inwardly extending rigid abutment portion to which said frangible portion is frangibly connected, said abutment portion being positioned to limit movement of said plunger means out of said distal end, thereby to limit movement of said end wall after said frangible portion is broken.

22. The syringe of claim 21 in which said barrel distal end is formed to provide means for retaining said end wall means after said frangible portion is broken.

23. The syringe of claim 13 in which said connecting means is positioned such that said plunger means and said end wall means are engaged and connected together before continued movement of said plunger means with said predetermined force breaks said frangible portion.

24. A syringe comprising a plastic barrel, a proximal end integrally molded to said plastic barrel, a distal end, an outwardly contoured end wall means closing said distal end, and an annular frangible portion joining said end wall means to said distal end, a movable plunger means reciprocably disposed in said barrel to drive fluid in said barrel toward and exiting out of said distal end when said plunger means is moved toward said distal end, said end wall means further being molded to have an outwardly extending cannula means hub with a central extending opening therethrough, a cannula means mounted on said hub to permit the driven fluid to exit out said distal end, said plunger means being formed to have an annular shoulder proportioned and shaped to engage said end wall means to break said frangible portion when said plunger means is moved toward said distal end with a predetermined force, and means for connecting said end wall means and said plunger means such that movement of said plunger means toward said proximal end will retract said end wall means and said cannula means within said barrel when said frangible portion has been broken; and wherein said connecting means is positioned such that said plunger means and said end wall means are engaged and connected together before continued movement of said plunger means with said predetermined force breaks said frangible portion; wherein said barrel distal end is further formed with an annular, radially inwardly extending rigid abutment portion to which said frangible portion is frangibly connected, said abutment portion being positioned to limit movement of said plunger means out of said distal end, thereby to limit movement of said end wall after said frangible portion is broken.

25. The syringe of claim 23 in which said plunger means is further formed with an outwardly contoured end generally conformingly to fit within said end wall means substantially fully to expel fluid from the barrel to the cannula means when said plunger means is moved against said end wall means.

26. The syringe of claim 25 in which said plunger means contoured end is formed at its radially outer edge to define said annular shoulder.

27. A syringe comprising
a barrel having a proximal end and a distal end, the proximal end including an interior wall formed to include outlet means for dispensing fluid from the barrel to a point of use, and
a movable plunger means reciprocable in the barrel to drive fluid in the barrel toward the distal end and the outlet means in the end wall, the plunger means including an exterior end wall configured to mate with the interior wall in close fitting relation upon engagement of the plunger means and the proximal end, and a protrusion attached to the exterior end wall and configured to engage the proximal end in the outlet means to connect the plunger means to the barrel, the protrusion being formed to include a passageway through which fluid in the barrel is conducted to reach the point of use upon occlusion of the outlet means by the protrusion in the outlet means and movement of the exterior end wall toward the interior wall.

28. The syringe of claim 27, wherein the protrusion includes an elongated stem attached to the exterior end wall and a ball mounted on a distal end of the elongated stem and the ball and stem are formed to include a slot defining said passageway.

29. The syringe of claim 28, wherein the interior wall of the fixed barrel and the exterior end wall of the reciprocable plunger means cooperate to define a fluid-receiving space therebetween having a volume that varies in proportion to the distance separating the interior wall and the exterior end wall, the stem is formed to include a first opening of the passageway communicating with the fluid-receiving space, and the ball is formed to include a second opening of the passageway.

* * * * *